United States Patent
Robinson et al.

(10) Patent No.: US 6,270,790 B1
(45) Date of Patent: Aug. 7, 2001

(54) SOFT, CONVEX SHAPED CHEWABLE TABLETS HAVING REDUCED FRIABILITY

(75) Inventors: Ronni L. Robinson, Ambler; James R. Damon, Chalfont; James R. Mossop, Quakertown; Michael D. Palmer, Philadelphia, all of PA (US)

(73) Assignee: MxNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/135,723

(22) Filed: Aug. 18, 1998

(51) Int. Cl.$^7$ .................. A61K 9/28; A61K 47/00
(52) U.S. Cl. ............ 424/441; 424/439; 424/489; 424/490; 424/493; 424/494; 424/497
(58) Field of Search ................. 424/464, 465, 424/494, 482, 470, 439, 441, 489, 490, 493, 497

(56) References Cited

U.S. PATENT DOCUMENTS

| | | |
|---|---|---|
| 3,619,292 * | 11/1971 | Brouillard et al. . |
| 4,760,094 * | 7/1988 | Blank et al. . |
| 4,851,226 * | 7/1989 | Julian et al. . |
| 5,075,114 | 12/1991 | Roche ........................ 424/470 |
| 5,275,823 * | 1/1994 | France et al. . |
| 5,460,825 * | 10/1995 | Roche et al. . |
| 5,464,632 | 11/1995 | Cousin et al. ............... 424/425 |
| 5,489,436 | 2/1996 | Hoy et al. .................. 424/441 |
| 5,609,883 | 3/1997 | Valentine et al. ........... 424/464 |
| 5,686,107 * | 11/1997 | Ratnaraj et al. . |
| 5,876,759 | 3/1999 | Gowan, Jr. .................. 424/494 |

FOREIGN PATENT DOCUMENTS

98/46215    10/1998  (WO) .

OTHER PUBLICATIONS

Muresan et al., Stability Study if Pyroxicam in the Presence of Auxiliary Substances of Compression, Farmacia 41, No. 1–2, pp. 51–56, 1993.*

Danckwerts et al., The Effect of Processing Variables in the Compression Properties of Controlled Release Core–In–Cup Compressed Tablets from a New Adjustable Punch, International Journal of Pharmaceutics, 123 pp. 85–94, 1995.*

Westerhuis et al., Optimisation of the Composition and Production of Mannitoll/Microcrystalline Cellulose Tablets, International Journal of Pharmaceutics, 143 pp. 151–162, 1996.*

Muntean et al., Formulation and Preparation of Some Chewable Tablets for Local Treatment of Bucco–Pharyngeal Infections, Farmacia 41, No. 1–2, pp. 51–56, 1993.*

(List continued on next page.)

Primary Examiner—Thurman K. Page
Assistant Examiner—Brian K. Seidleck
(74) Attorney, Agent, or Firm—Bernard F. Plantz

(57) ABSTRACT

The present invention relates to a compressed, chewable tablet containing at least one active ingredient, a water-disintegratable, compressible carbohydrate and a binder. These components are dry blended and compressed into convex-shaped tablet having a hardness of about 2 to about 11 kp/cm$^2$ and friability less than 1%.

8 Claims, 2 Drawing Sheets

OTHER PUBLICATIONS

Figure 1A:
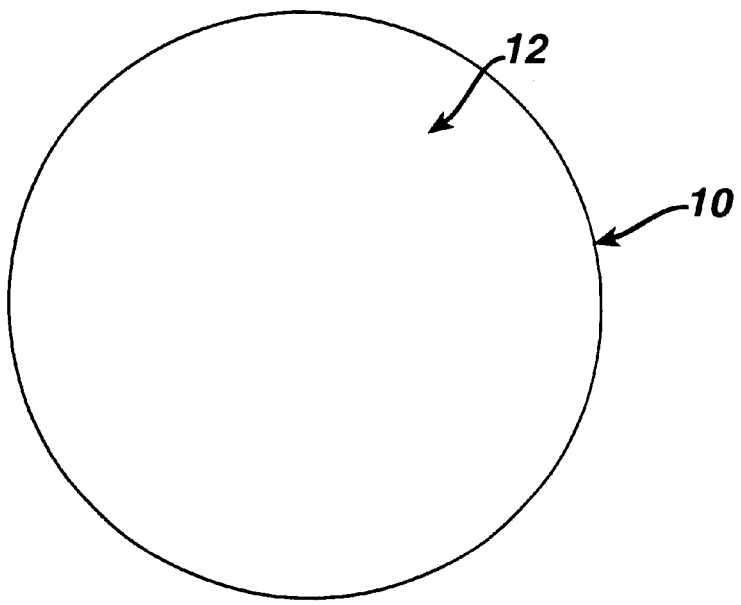

Ambros et al., The Characterization of the Mechanical Strength of Chewable Tablets, Pharm. Develop. Technol. 3, No. 4 pp. 509–15, 1998.*

Morris et al., Characterization and Performance of a New Direct Compression Excipient for Chewable Tablets: Xylitab, Drug Dev. Ind. Pharm., 22, No. 9–10 pp. 925–32, 1996.*

Pitt et al., J. Pharm. Pharmacol., vol. 41, p. 289–292 (1989).

Gold et al., Journal of Pharmaceutical Sciences, vol. 69, No. 4, p. 384–386 (1980).

Gold et al., Pharmaceutical Technology, Dec. 1983, p. 31–38 and 71 (1983).

Sugimori et al. Powder Technology, vol. 58, p. 259–264 (1989).

Chakrabarti et al. The Indian Journal of Pharmacy, vol. 37, No. 3, p. 62–65 (1975).

J. Pharm. Pharmac., vol. 24, p. 503–504 (1992).

Aulton, M.E., Pharm. Helv. vol. 56, No. 12, p. 332–6 (1981).

Hwang et al. Drug Development and Industrial Pharmacy, vol. 19, No. 5, p. 507–19 (1973).

Horikoshi, et al. Chem. Pharm. Bull., vol. 21, No. 10, p. 2136–40 (1973).

Pitt et al., J. Pharma. Pharmacol., vol. 42, p. 219–225 (1990).

Chowhan et al. Journal of Pharmaceutical Sciences, vol. 81, No. 3, p. 290–94 (1992).

Leonard et al., Drug Development and Industrial Pharmacy, vol. 15, No. 3, p. 434–359 (1989).

Kigasawa et al. Yakugaku Zasshi, vol. 95, No. 7, p. 769–773 (1975).

* cited by examiner

SOFT, CONVEX SHAPED CHEWABLE TABLETS HAVING REDUCED FRIABILITY

FIELD OF THE INVENTION

The present invention relates to soft, convex-shaped compressed chewable tablets and a process for preparing such tablets.

BACKGROUND OF THE INVENTION

Chewable tablets are widely used in the pharmaceutical industry for patients, such as children, who have who have difficulty swallowing conventional tablets or capsules. Children's TYLENOL® Chewable Tables are an example of a pediatric chewable acetaminophen tablet sold in the United States. These tables are packaged in bottles and have a flat face, beveled edge shape. Samples of these tablets obtained from retail locations had hardnesses (average of ten tablets) ranging from 5.3–13.1 kp or normalized hardnesses of 12.3–30.5 kp/cm$^2$.

Many comercially avaialable pediatric chewable tablets contain active ingredients which are coated with polymers to mask their unpleasant taste. However, the forces used to compress these tablets can fracture the polymer coatings, which reduces the effectiveness of the tastemasking system.

Rapidly disintegrating dosage forms, such as those described in U.S. Pat. No. 5,464,632, issued Nov. 7, 1995, are also available for patients, particularly aged and pediatric patients, having difficluties swallowing tablets and caplets. However, rapidly disintegrating dosage forms currently available are highly friable, and require the use of special handling and costly packaging, e.g., specially designed blister packs, to prevent breakage or chipping of the tablets. These limitations significantly increase the product cost.

Tablet shape also affects tablet friability. T. Chakrabarti et al. in *The Indian Journal of Pharmacy,* Vol. 38, No. 3, pp. 62–65 (1975) disclose that lower friability was observed in beveled flat tablets followed by standard convex and plain flat tablets. Similarily, K. Sugimori et al. in *Powder Technology*, Vol. 58, pp. 259–264 (1989) report that capping occurs more often in convex-shaped tablets than flat faced tablets.

A need, therefore, exists for compressed, chewable tablets having improved taste, but which exhibit low friability so that they may be processed with standard bulk handling equipment and packaged in bottles.

SUMMARY OF THE INVENTION

The present invention provides a compressed, chewable tablet containing at least one active ingredient, a water-disintegratable, compressible carbohydrate and a binder. These components are dry blended and compressed into a convex-shaped tablet having a hardness of about 2 to about 11 kp/cm$^2$. The tablet has a friability of less than 1%.

In a preferred embodiment of the present invention, the compressed, chewable tablet is prepared by dry blending the active ingredient, water-disintegratable, compressible carbohydrate and binder, and then compressing into a convex-shaped tablet having a hardness of about 2 to about 11 kp/cm$^2$. If the active ingredient has an objectionable taste, it is coated with a taste masking composition.

Compressing at reduced force reduces fracture of the coating used for masking the unpleasant taste of the active ingredient. These convex-shaped, chewable tablets are softer that conventional chewable tablets, which results in improvements in product taste, mouthfeel, and ease of chewing.

The convex tablet geometry significantly reduces tablet friability at a given compression force. This reduction in tablet friability allows for the use of lower compression forces and lower tablet hardness, while maintaining the ability to process the tablets with conventional bulk handling equipment and package them in conventional bottles.

BRIEF DESCRIPITON OF THE DRAWINGS

Figure 1B:
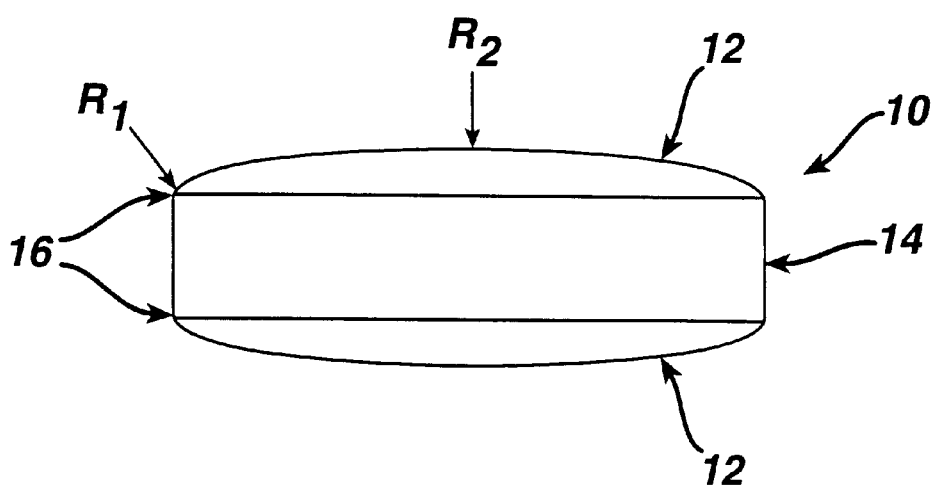

FIGS. 1*a* and 1*b* are front and side views, respectively, of a bi-convex tablet of the present invention.

Figure 2:
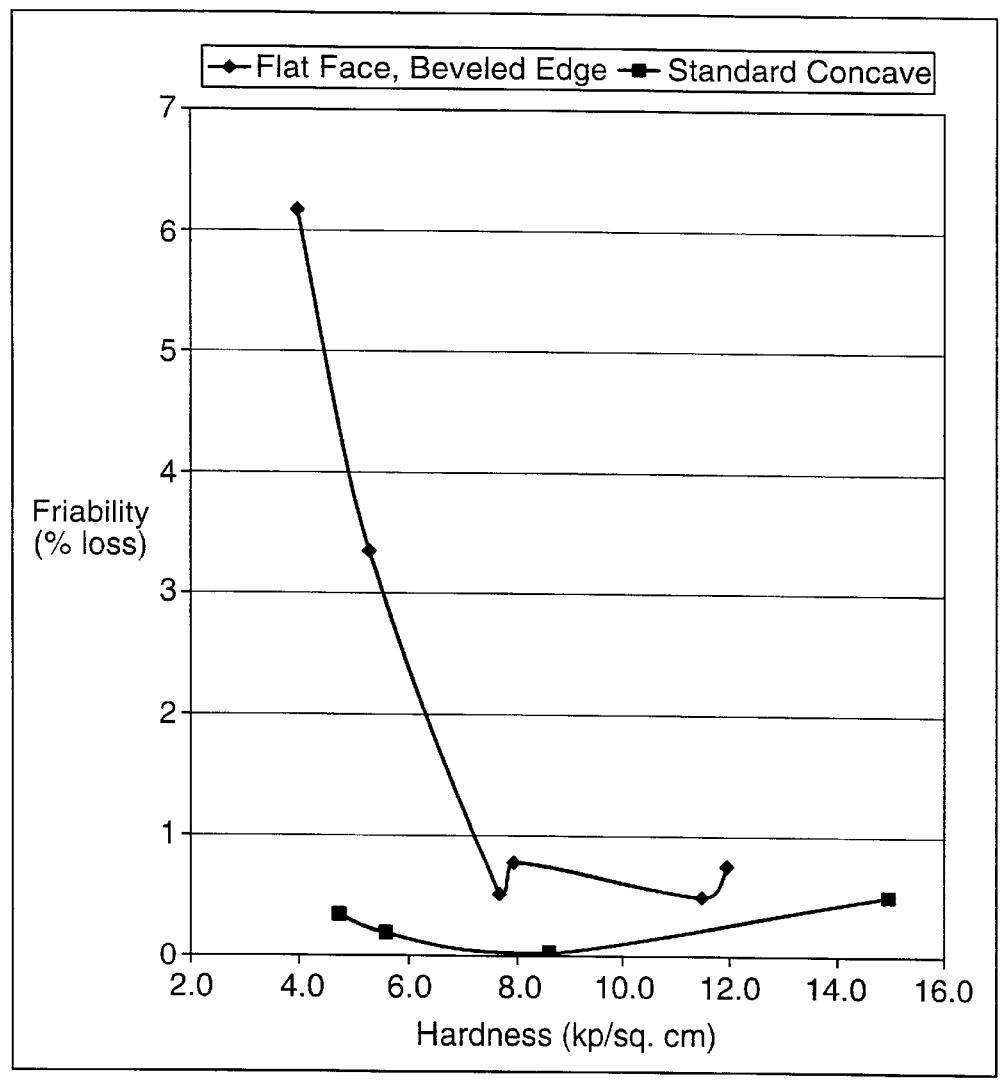

FIG. 2 is a graph of friability (wt % loss) vs. hardness (kp/cm$^2$) for a flat face, beveled edge tablet (control) and a concave tablet of the present invention.

DETAILED DESCRIPTION OF THE PREFERRED EMBODIMENTS

The compressed, chewable tablets of the present invention comprise at least one active ingredient, a water-disintegratable, compressible carbohydrate, and a binder. These ingredients are dry blended and then compressed into a convex-shaped tablet having a hardness of about 2 to about 11, preferably about 5 to about 8.5, kp/cm$^2$. Tablet friability is also preferably less than 1%.

Tableting machines, preferably those capable of applying separate pre-compression and main compression forces, are used to compress the ingredients into tablets. Since the ingredients are dry blended, water-soluble, as well as water-insoluble, active ingredients can be used in the tablet. If the active ingredients have an objectionable taste they may be coated with a taste masking composition.

The water-disintegratable, compressible carbohydrate used in the present invention includes carbohydrate materials conventionally used in tablets. The carbohydrates facilitate the breakup of the dosage form after oral administration, and are described in Lieberman et al., *Pharmaceutical Dosage Forms*, Marcel Dekker, Inc., New York, 2 Ed. Vol. 1, pp. 205–209 (1990), which is hereby incorporated by reference. Preferred water-disintegratable, compressible carbohydrates include mannitol, sorbitol, maltitol, dextrose, sucrose, xylitol, lactose, and mixtures thereof.

The binder in the present invention is used to add cohesiveness to the formulation, thereby providing the necessary bonding to form a cohesive mass or compact upon compression. These binders are conventionally used in direct compression tablets and are described in Lieberman et al., *Pharmaceutical Dosage Forms,* 2 Ed., Vol. 1, pp. 209–214 (1990), which is hereby incorporated by reference. Preferred binders include cellulose, cellulosic derivatives, polyvinyl pyrrolidone, starch, modified starch, and mixtures thereof, and, in particular, microcrystalline cellulose available from FMC Corp. under the trademark AVICEL® PH 101.

The tablets of the present invention are used to orally administer a wide variety of active ingredients. Suitable active ingredients include pharmaceuticals, minerals, vitamins and other nutraceuticals. Suitable pharmacuticals include analgesics, decongestants, expectorants, antitussives, antihistamines, gastrointestinal agents, diuretics, bronchodilators, sleep-inducing agents and mixtures thereof. Preferred pharmaceuticals include acetaminophen, ibuprofen, flurbiprofen, naproxen, aspirin, pseudoephedrine, phenylpropanolamine, chlorpheniramine maleate, dextromethorphan, diphenhydramine, famotidine, loperamide, ranitidine, cimetidine, astemizole, terfenadine, terfenadine carboxylate, cetirizine, mixtures thereof and pharmaceutically acceptable salts thereof.

The active ingredients are present in the tablet in a therapeutic effective amount, which is an amount that produces the desired therapeutic response upon oral administration and can be readily determined by one skilled in the art. In determining such amounts, the particular compound being administered, the bioavailability characteristics of the ingredient, the dose regime, the age and weight of the patient, and other factors must be considered.

If the active ingredient has an objectionable taste, a coated particle containing the active ingredient coated with a taste masking coating is employed. The active may be coated with taste masking coatings known in the art, such as those described in U.S. Pat. No. 4,851,226, issued Jul. 25, 1989, to T. W. Julian, et al.; U.S. Pat. No. 5,075,114, issued Dec. 24, 1991 to E. J. Roche; and U.S. Pat. No. 5,489,436, issued Feb. 6, 1996, all of which are hereby incorporated by reference. Commercially available taste masked active ingredients may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

As used in the present invention, "coated particle" refers to a solid active ingredient in the form of a crystal or particle, an agglomerate of individual particles, or a granulated particle, which has been encapsulated with a the taste masking composition, either by film coating or by another process such as coaccervation. The tablet may provide for immediate or sustained release of the active.

Taste masking compositions suitable for use as coatings are provided in the following table:

| Polymer System | Coat Level[1] | Polymer Ratio[2] |
|---|---|---|
| Cellulose Acetate/PVP | 5–60% | 90/10 to 60/40 |
| Cellulose Acetate Butyrate/PVP | 5–60% | 90/10 to 60/40 |
| Cellulose Acetate/HPC | 5–60% | 90/10 to 50/50 |
| Cellulose Acetate Butyrate/HPC | 5–60% | 90/10 to 50/50 |
| Cellulose Acetate/ EUDRAGIT E100 | 8–60% | All ratios |
| Cellulose Acetate Butyrate/ EUDRAGIT E100 | 8–60% | All ratios |
| Ethyl Cellulose/PVP | 8–60% | 90/10 to 60/40 |
| Ethyl Cellulose/HPC | 8–60% | 90/10 to 50/50 |
| Ethyl Cellulose/ EUDRAGIT E100 | 8–60% | All ratios |
| HPC | 10–60% | NA |
| HEC | 10–60% | NA |
| EUDRAGIT E100 | 10–60% | NA |
| HPMC | 10–60% | NA |
| HEC/HPMC | 10–60% | All ratios |
| HPC/HPMC | 10–60% | All ratios |
| HEC/HPC | 10–60% | All ratios |
| 2-vinyl pyrridine styrene co-polymer | 10–60% | NA |
| CA/2-vps | 8–60% | All ratios |
| CAB/2-vps | 8–60% | All ratios |
| Ethyl Cellulose/2-vps | 8–60% | All ratios |
| Cellulose Triacetate/PVP | 8–60% | 90/10 to 60/40 |
| Cellulose Triacetate/HPC | 8–60% | 90/10 to 50/50 |
| Cellulose Triacetate/ EUDRAGIT E100 | 8–60% | All ratios |
| HEC — Hydroxyethyl cellulose | | |
| HPMC — Hydroxypropylmethyl cellulose | | |
| CA — Cellulose Acetate | | |
| CAB — Cellulose Acetate Butyrate | | |
| 2-VPS — 2-Vinyl pyridine styrene | | |
| EUDRAGIT ™ E-100 — methylaminoethyl-methacrylate and neutral methacrylic acid esters available from Rohm Pharma GmbH, Germany. | | |

[1] Percent by weight of the coated particle in a dried state.
[2] By weight.
PVP — polyvinylpyrrolidone
HPC — Hydroxypropyl cellulose Substantially all of the active ingredient or granulated active ingredient should be coated with a layer of a taste masking composition having a thickness of about 3 to about 10 microns. The coating should be substantially free of cracks, holes or other imperfections when examined under a scanning electron microscope at 100–500×.

If taste masking is necessary, the active ingredient is preferably coated with a blend of a first polymer selected from the group consisting of cellulose acetate and cellulose acetate butyrate and a second polymer selected from the group consisting of polyvinyl pyrrolidone and hydroxypropyl cellulose. The weight ratio of the first polymer to the second polymer in this blend is within the range of about 90:10 to about 50:50 and preferably about 90:10 to about 70:30.

The blend of first and second polymers may be coated directly onto the pure active ingredient or may be coated onto a granulated particle containing the active. In the case of a granulated particle, such as a rotogranulated particle, the active will constitute from about 5 to about 90 weight percent of the particle, with the remainder being the binder or filler. Suitable binders for the granulated particles include polyvinyl pyrrolidone, hydroxypropylmethyl cellulose, hydroxypropyl cellulose, and other pharmaceutically acceptable polymers. Fillers suitable for use in such granulated particles include lactose, confectioner's sugar, mannitol, dextrose, fructose, other pharmaceutically acceptable saccharides and microcrystalline cellulose.

The coated particles may be prepared by spraying an organic solvent solution of the polymeric blend onto the active ingredient, or a granulated particle containing the active ingredient, in a fluidized bed, such as a Wurster coater or a rotogranulator. A wide variety of organic solvents may be used to prepare the solution of the polymeric blend. For example, a preferred solvent is a mixture of acetone and methanol, but other solvent systems may be employed, including methylene chloride, methylene chloride-methanol, acetone-ethyl acetate, toluene-ethanol and acetone-ethanol. Generally, the proportion of the polymer blend in the solvent solution will be within the range of about 5 to about 20, preferably about 8 to about 15, weight percent, depending on the solvent and other similar considerations.

When a fluidized bed coating operation is used, air, which may be heated, passes through a bed of the active ingredient solids to fluidize them, and the solution of the polymeric blend is sprayed onto the fluidized bed and thereby coats the active. The air passing through the bed dried the coating onto the active ingredient, so that a dry coated granule is obtained.

Conventional fluidized bed coating equipment may be used in the present invention to coat the active ingredient or the rotogranulated particle containing the pharmaceutical. This equipment includes Wurster fluid-bed coaters, where the solution of the polymer blend is sprayed from the bottom of the chamber, and a rotogranulator, where the solution of the polymer blend is tangentially sprayed. These coating operations are further described in Lieberman et al., *Pharmaceutical Dosage Forms*, Marcel Dekker, Inc., New York, Vol. 3, pp. 138–150 (1990), which is hereby incorporated by reference.

The coated particle, in a dried state, generally contains about 5 to about 60, preferably about 10 to 40, weight percent of the blend of the first and second polymers. The exact proportions of the coating to the active ingredient can, however, vary depending upon the level of taste masking required and whether a sustained or immediate release of the active is desired. Larger proportions of the coating tend to provide a sustained release effect and enhance taste masking.

The tablet may also contain ingredients other than the coated particles, carbohydrate and binder. The additional ingredients include sweeteners, such as aspartame, acesulfame potassium, sucralose and saccharin; and lubricants, such as magnesium stearate, stearic acid, talc, and waxes. The dosage form may also incorporate pharmaceutical acceptable adjuvants. Such adjuvants, include, for example, preservatives, flavors, antioxidants, surfactants, and/or colors.

The tablets, on a dry basis, generally comprise from about 0.1 to about 60, preferably about 12 to about 25, percent by weight of the active ingredient; from about 30 to about 90, preferably about 40 to about 65, percent by weight of the water-disintegratable, compressible carbohydrate material; from about 1 to about 30, preferably about 5 to about 20, percent by weight of the binder; from about 0.1 to about 5, preferably about 0.5 to about 1.5, percent by weight of the lubricant; from 0 to about 5, preferably about 0.1 to about 3.0, percent by weight of the sweetener; from 0 to about 5, preferably about 0.2 to about 2.0, percent by weight of the flavor; and from 0 to about 5, preferably about 0.01 to about 0.4, percent by weight of the color.

The unit weight of the tablet will vary depending on the dosage of the active ingredient. The unit weight will generally range from about 250 to about 1000 mg. A typical dosage form may contain:

| Ingredient | Unit Wt. (mg) |
| --- | --- |
| Active Ingredient | 0.5–600 |
| Compressible Carbohydrate | 80–900 |
| Binder | 10–200 |
| Lubricant | 1–15 |
| Sweetener | 0–30 |
| Flavor | 0–20 |
| Color | 0–10 |

If taste masking is required, coated particles of the active ingredient are prepared using the aforementioned techniques. The particle size of the coated particles, as well as the remaining components, is generally less than 600 microns. The components of the tablet are then dry mixed to form a uniform powder blend. The blend is then compressed into a tablet of the desired hardness using conventional compression tableting techniques.

In a preferred embodiment of the invention, the compressed, chewable tablet has a convex or bi-convex shape and is relatively soft so as to provide good mouthfeel and taste and ease of chewing. Generally, the tablet will have a diameter of about 7 to about 19, preferably about 9 to about 13, mm and a thickness of about 2 to about 12, preferably about 3 to about 8, mm.

FIGS. 1a and 1b are, top and side views, respectively, of a bi-convex tablet of the present invention. The tablet 10 has a pair of opposed face surfaces 12 and a side surface 14. The intersection of the face surfaces 12 with the side surface 14 defines the edges 16. The face surfaces 12 for the bi-convex tablet 10 have two radii of curvature, $R_1$ and $R_2$. The radius of curvature $R_1$ at the portion of the face surface 12 proximate to the edge 16 (minor axis cup radius) is about 0.7 to about 7.6, preferably about 2.36, mm. The radius of curvature $R_2$ at the center of the tablet face 12 (major axis cup radius) is about 7 to about 76, preferably about 25.2, mm. Alternatively, the minor axis cup radius $R_1$ is about 10% to about 40% of the tablet diameter, while the major axis cup radius $R_2$ is about 100% to about 400% of the tablet diameter. The radius of curvature of the face surface of a simple convex tablet of the present invention (not shown) is about 5 to about 60 mm, which is about 75% to about 300% of the tablet diameter. Tri-convex tablets may also be used.

The external pressure applied by the tablet press during the compression step is controlled so that the hardness of the tablet is within the range of about 2 to about 11, preferably about 5 to about 8.5, kiloponds (kp) per sq. cm ($cm^2$). Tablet breaking strength, or hardness, is dependent on cross-sectional area at the tablet breaking point. In order to compare values across different size tablets, the breaking strength must be normalized for the area of the break. This normalized value, expressed in $kp/cm^2$, is often referred in the art as tablet tensile strength. Hardness is measure by conventional pharmaceutical hardness testing equipment, such as a Schleuniger Hardness Tester.

During tableting it is preferable to apply the compression forces in two steps. A pre-compression pressure of about 2 to about 17, preferably about 5.5 to about 11.5, $kN/cm^2$ is applied. The main compression pressure of about 3 to about 18, preferably about 7 to about 13, $kN/cm^2$ is then applied to complete the compression operation. Alternatively, the tablet may be formed in one compression step using a compression pressure of about 3 to about 18, preferably about 7 to about 13, $kN/cm^2$.

The compressed, chewable tablet has a friability of less than 1%, preferably less than 0.5%. In the present invention, tablet friability is determined in accordance with USP Method <1216> Tablet Friability, USP 23 (1995) and is expressed as percent weight loss. As shown in FIG. 2, as the hardness of a flat face, beveled edge tablet is reduced, friability increases. However, when the hardness of a concave tablet of the present decreases, friability remains substantially constant. These findings are unexpected in view of the friability reported by Chakrabarti et al. and Sugimori et al., supra, for convex tablets.

These findings are significant because the tablets of the present invention can be compressed at lower compression forces, but still maintain acceptable friability. This results in a softer tablet having improved product taste, mouthfeel and ease of chewing. Compressing at reduced forces also reduces the probability of fracturing the coating used for masking the unpleasant taste of the active ingredient.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE I

This Example provides a formulation for making a compressed, chewable bi-convex tablet containing acetaminophen coated with a blend of cellulose acetate and polyvinyl pyrrolidone. The weights provided hereinafter are based on a tablet unit weight of 385 mg.

A coating solution containing a blend of cellulose acetate and polyvinyl pyrrolidone was prepared in accordance with U.S. Pat. No. 4,851,226 and applied to acetaminophen until coated acetaminophen particles containing approximately 11% by weight of coating were obtained. The ratio of cellulose acetate to polyvinyl pyrrolidone was 85:15.

The coated acetaminophen particles were combined with following ingredients to produce the tablets:

| Ingredients | Unit Wt. (mg) |
|---|---|
| CA/PVP Coated Acetaminophen Particles | 89.9 |
| Mannitol (Granular), USP | 246.03 |
| Microcrystalline Cellulose, NF | 30.0 |
| Aspartame, NF | 9.0 |
| Color | 1.27 |
| Citric Acid, USP | 2.1 |
| Flavor | 2.3 |
| Magnesium Stearate, NF | 4.4 |
| Tablet weight | 385.0 |

Procedure
1. Citric acid, aspartame, and color were combined with a portion of microcrystalline cellulose, and blended until a uniform distribution of color was obtained. This blend was then passed through a suitable comminutor.
2. Magnesium stearate and a portion of the mannitol were combined and passed through a suitable comminutor.
3. The remaining mannitol was passed through a suitable comminutor and then discharged into a blender.
4. The blends from 1 and 2 above, flavor, coated acetaminophen, and the remainder of the microcrystalline cellulose were added to the blender, and blended until uniform distribution of active ingredient was achieved.
5. The blend was compressed into bi-concave tablets to the following specifications on a Fette Model 3090 rotary tablet press:
   Punches: 10.3 mm diameter, bi-concave having a minor axis cup radius of curvature of 2.36 mm and a major axis cup radius of curvature of 25.2 mm
   Pre-compression Force: 7.4–8.1 kN (8.5–9.4 kN/cm$^2$)
   Main Compression Force: 8.4–9.1 kN (9.7–10.6 kN/cm$^2$)
   Thickness: Target 4.5 mm
   Weight: Target 385 mg
   Friability*: Target 0.14

The following measurments were made on the tablets:

| Physical Property | Average of 5 | Individuals |
|---|---|---|
| Weight (mg) | 382–389 | 379–391 |
| Hardness (kp/cm$^2$) | 6.0–7.4 | 5.2–8.3 |
| Thickness (mm) | 4.44–4.49 | 4.43–4.52 |
| Friability* | — | 0.11–0.18 |

*(% wt. loss, 20 tablets)

Bulk tablets were successfully transported between Puerto Rico and New Jersey in 19-gallon fiber drums containing approximately 30 kg of tablets per drum.

EXAMPLE II

This Example describes the friability testing reported in FIG. 2 for the flat face, beveled edge (FFBE) tablet (control) and the concave tablet of the present invention. The acetaminophen was coated with the taste masking coating described in Example I.

The coated acetaminophen particles were combined with following ingredients to produce the FFBE and concave tablets:

| | Unit Wt. (mg) | |
|---|---|---|
| Ingredients | Concave | FFBE |
| CA/PVP Coated Acetaminophen | 90.7 | 90.7 |
| Mannitol (Granular), USP | 241.55 | 226.55 |
| Microcrystalline Cellulose, NF | 30.0 | 30.0 |
| Aspartame, NF | 5.0 | 11.0 |
| Acesulfame Potassium | 6.0 | — |
| Color | 0.35 | 0.35 |
| Flavor | 22.5 | 22.5 |
| Magnesium Stearate, NF | 3.9 | 3.9 |
| Tablet Weight | 400.0 | 385.0 |

The ingredients were blended and compressed into tablets on a Manesty Betapress at different hardness levels by changing the compression forces. The following specifications were used:
Concave
   Punches: Round, no land, standard concave 13/32 inch (10.3 mm)×0.038 inch cup depth
   Hardness Range: 1.5–6.0 kp
   Weight(10 tablets): 4.0 g (Range 3.85–4.15 g)
FFBE
   Punches: 10 mm round flat faced, beveled edge
   Hardness Range: 1.5–6.0 kp
   Weight (10 tablets): 3.85 g (Range 3.75–3.95 g)

The friability of the tablets was measured in accordance with Tablet Friability <1216>, USP 23 (1995). Friabilty in wt % was then plotted against normalized hardness or tablet tensile strength in FIG. 2.

EXAMPLE III

Tastemasked acetaminophen particles, prepared in the manner described in Example I, were combined with the following ingredients to produce compressed, chewable tablets, using the process described below:

| Ingredients | Unit Wt. (mg) | |
|---|---|---|
| CA/PVP Coated Acetaminophen Particles | 90.7 | |
| Mannitol (Granular), USP | 243 | 96 |
| Microcrystalline Cellulose, NF | 30.0 | |
| Aspartame, NF | 11.0 | |
| Color | 0.04 | |
| Citric Acid, USP | 2.1 | |
| Flavor | 3.3 | |
| Magnesium Stearate, NF | 3.9 | |
| Tablet Weight | 385.0 | |

Procedure
1. All ingredients except magnesium stearate were combined in a PK blender, and blended for 10 minutes. The magnesium stearate was added to the blender and blending was continued for an additional 5 minutes.
2. Tablets were compressed to the following specifications on a Manesty Betapress using 13/32-inch diameter, round bi-concave tooling having 2.36 mm minor axis cup radius and 25.2 mm major axis cup radius:

Target
Pre-compression Force 0–0.1 kN (0–0.12 kN/cm$^2$)
Main compression Force 6.5–6.9 kN (7.5–8.0 kN/cm$^2$)
Weight (average of 10): 385 mg
Thickness (average of 5): 4.63 mm
Hardness (average of 5): 3.0 kp(6.5 kp/cm$^2$)

The following measurements were made on the tablets:

| Physical Property | Range |
| --- | --- |
| Weight (average of 10) | 383.5–386.7 mg |
| Hardness (average of 5) | 2.90–3.06 kp (6.27–6.61 kp/cm$^2$) |
| Thickness (average of 5) | 4.62–4.66 mm |

A sensory preference test was conducted among 130 adults who tasted these tablets in comparison with Children's TYLENOL® 80 mg Acetaminophen Chewable Tablets (having an average hardness of 5.5 kp or 13.4 kp/cm$^2$ obtained from retail locations. The tablets in this example were preferred over the commercial product by 77% of the participants, while 22% preferred the commercial product. The tablets in this example were perceived as less bitter, more sweet, and having more pleasant taste and mouthfeel than the commercial product.

Various modifications can be made from the above-described embodiments without departing from the spirit and scope of the present invention.

What is claimed is:

1. A compressed, chewable tablet having opposed major surfaces, comprising:
   about 0.1 to about 60% of at least one active ingredient coated with a taste masking coating;
   about 30 to about 90% of a water-disintegratable, compressible carbohydrate selected form the group consisting of mannitol, sorbitol, maltitol, dextrose, sucrose, xylitol, lactose, and mixtures thereof;
   about 1 to about 30% of a binder selected form the group consisting of cellulose, cellulosic derivatives, polyvinyl pyrrolidone, starch, modified starch and mixtures thereof;
   about 0.1 to about 5% of a lubricant;
   0 to about 5% sweetener;
   0 to about 5% flavor;
   0 to about 5% color, by weight of said tablet; and
   said face surfaces having a convex shape and said tablet having a hardness of about 2 to about 11 kp/cm$^2$ and a friability of less than about 1%.

2. The tablet of claim 1 having a hardness of about 5 to about 8.5 kp/cm$^2$.

3. The tablet of claim 1 having a friability of less than about 0.5%.

4. The tablet of claim 1 wherein said face surfaces have a bi-convex or tri-convex shape.

5. The tablet of claim 4 having bi-convex shaped face surfaces and a minor axis cup radius of about 10 to about 40 percent of the tablet diameter and major axis cup radius of about 100 to about 400 percent of the tablet diameter.

6. The tablet of claim 1 wherein said coated active ingredient comprises at least one active ingredient coated with a blend of a first polymer selected from the group consisting of a cellulose acetate and cellulose acetate butyrate and a second polymer selected from the group consisting of polyvinyl pyrrolidone and hydroxypropyl cellulose, wherein the weight ratio of the first polymer to the second polymer is within the range of about 90:10 to about 50:50.

7. The tablet of claim 6 wherein the coated active ingredient comprises about 5 to about 60 percent by weight of the blend of first and second polymers.

8. The tablet of claim 1 wherein the active ingredient is selected from the group consisting of acetaminophen, ibuprofen, flurbiprofen, naproxen, aspirin, pseudoephedrine, phenylpropanolamine, chlorpheniramine maleate, dextromethorphan, diphenhydramine, famotidine, loperamide, ranitidine, cimetidine, astemizole, terfenadine, terfenadine carboxylate, cetirizine, mixtures thereof and pharmaceutically acceptable salts thereof.

* * * * *